(12) United States Patent
Cheng et al.

(10) Patent No.: US 9,073,967 B2
(45) Date of Patent: Jul. 7, 2015

(54) HIGH SALT-RESISTANCE ANTIBACTERIAL PEPTIDE AND METHOD FOR PRODUCING THE SAME

(75) Inventors: Jya-Wei Cheng, Hsinchu (TW);
Hui-Yuan Yu, Hsinchu (TW);
Hsi-Tsung Cheng, Hsinchu (TW);
Kuo-Chun Huang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 163 days.

(21) Appl. No.: 13/471,688

(22) Filed: May 15, 2012

(65) Prior Publication Data

US 2013/0109834 A1 May 2, 2013

(30) Foreign Application Priority Data

Oct. 26, 2011 (TW) .............................. 100138970 A

(51) Int. Cl.
| | |
|---|---|
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 7/08* | (2006.01) |

(52) U.S. Cl.
CPC ........................................ *C07K 7/08* (2013.01)

(58) Field of Classification Search
None
See application file for complete search history.

(56) References Cited

U.S. PATENT DOCUMENTS 6,528,488 B2 * 3/2003 Spacciapoli et al. ........... 514/1.8

FOREIGN PATENT DOCUMENTS

WO    WO9640770    * 12/1996 ............. C07K 14/47

OTHER PUBLICATIONS

Wei et al. Solution Structure of a Novel Tryptophan-Rich Peptide with Bidirectional Antimicrobial Activity. J Bacteriol. Jan. 2006, vol. 188, No. 1, pp. 328-334.*
Betts et al. Amino Acid Properties and Consequences of Substitutions. Bioinformatics for Geneticists. Chapter 14. 2003, pp. 289-316.*
Yu, H.-Y., Tu, C.-H., Yip B.-S., Chen, H.-L., Cheng, H.-T., Huang, K.-C., Lo, H.-J., Cheng, J.-W., "Easy Strategy to Increase Salt Resistance of Antimicrobial Peptides," Antimicrobial Agents and Chemotherapy, Oct. 2011, p. 4918-4921.

* cited by examiner

*Primary Examiner* — Marcela M Cordero Garcia
(74) *Attorney, Agent, or Firm* — Muncy, Geissler, Olds & Lowe, P.C.

(57) ABSTRACT

The present invention is related to a high salt-resistance antibacterial peptide by increasing width of side chain of amino acids and/or increasing length of side chain of amino acids in the antibacterial peptide; and a method for increasing salt-resistance of antibacterial peptide by increasing width of side chain and/or increasing length of side chain in the antibacterial peptide.

5 Claims, 3 Drawing Sheets

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Syntheized Sequence

<400> SEQUENCE: 1

Ala Lys Arg His His Gly Tyr Lys Arg Lys Phe His
1               5                   10

HIGH SALT-RESISTANCE ANTIBACTERIAL PEPTIDE AND METHOD FOR PRODUCING THE SAME

CROSS-REFERENCE TO RELATED APPLICATIONS

This Non-provisional application claims priority under 35 U.S.C. §119(a) on Patent Application No(s). [100138970] filed in Taiwan, Republic of China [Oct. 26, 2011], the entire contents of which are hereby incorporated by reference.

FIELD OF THE INVENTION

The present invention relates to a high salt-resistance antibacterial peptide and a method for increasing the salt resistance of an antibacterial peptide, especially related to increase the salt-resistance by increasing the width of a side chain of a hydrophobic terminal in an amino acid and/or by increasing the length of a side chain of a hydrophobic terminal in an amino acid.

BACKGROUND OF THE INVENTION

As for the generating of drug-resistance microorganism by traditional antibiotics, many research focused on new therapeutic reagent, including many antibiotic peptides generated from animals. Antimicrobial peptides play important roles in the host innate defense mechanism by interacting and permeabilizing microbial membranes. The antibacterial peptides possibly exist in some plants, insects, Amphibia and mammals. The antibiotic of antibacterial peptides can fight against bacteria, fungus and even some virus. This kind of antibacterial peptide binds with lipid (more than 95%) and breaks the integrity of the membrane by departing of the lipid bilayer rapidly. On the other hand, it can add a small and short transportation on parallel lipid bilayer of the bacteria, so as to depolarize the cell membrane and break the original voltage gradient.

This kind of antibacterial peptide performs defensive protection function in host, which has been proved in fruit fly. When the fruit fly was infected by microbes and the expression of antibacterial peptide decrease, the survival rate of the fruit fly will decrease significantly. However, in mammals, it has been proved that this kind of antibacterial peptide performs defective protection function in defective bacterial killing of patients and mice with Cystic fibrosis. The antibacterial peptides which were found in mammals can be classified as cysteine-rich defensins and a variety of cathelicidin.

Cathelicidin contains a highly preserved signal sequence and a pre-area cathelin and the variation antibacterial sequence on C-terminal area. Many cathelicidin have unique cutting site on elastin protein kinase between negative charged cathelin area and positive charged c-terminal area. The protein hydrolysis reaction of the cutting site is observed and is necessary as antibacterial activity in neutrophil in cattle and pig. According to the contents and structures of the amino acids, the cathelicidin family can be classified into three groups: first group is having hydrophilic helix structure, such as LL-37, CRAMP, SMAP-29, PMAP-37, BMAP-27 and BMAP-28; and the second group is Arginine/Proline or Tryptophan-rich peptide, such as Bac5, Bac7, PR-39 and indolicidin; The third group is Cysteine-rich peptide, such as protegrins.

In academy, the non-antibiotic microbe therapy, such as the type of antibacterial peptide, could be the main axis of development in antibacterial drug in the future. Especially, the drug-resistance is becoming severer, it is utility for industry as a therapy for fishing farming and animal farming. It is hopeful to solve the secret worry coming from the overflow of antibiotic today.

SUMMARY OF THE INVENTION

Most antibacterial peptides are positive charged, for example, the P113 which is belonged to a-helix peptide in FIG. 2 is with hydrophilic terminal (12) and hydrophobic terminal (11). The hydrophilic terminal would associate with the bacteria membrane and the hydrophobic terminal would insert into the antigen. The invasion and causing of the death of microbes is showed in FIG. 1. The P113 would interfere the cell membrane of the microbes and the inner membrane of the microbes by insert into the surface from outside of the microbes (101).

However, the antibacterial peptide is a biological macromolecule, which is produced and secret by specific part of the organism. The physiological environment such as salt concentration, pH value, etc., is limited to certain degree, so as to limit the usage scope and effect. Therefore, moderate modifying the amino acids of this kind of peptide is helpful on medical field, applicable environmental field and general adaptive for development of formulation, so as to evaluate the therapeutic effect in high salt concentration environment. The present invention is related to developing a high-salt resistance antibacterial peptide and a method for increasing the salt resistance of antibacterial peptide, so as to solve the general problems in antibacterial peptides nowadays.

Accordingly, one aspect of the present invention is to provide a high salt-resistance antibacterial peptide and the method of producing thereof.

For the purpose, the present invention provides a high salt-resistance antibacterial peptide, wherein a side chain of a hydrophobic terminal of an amino acid is increased by width and/or a side chain of a hydrophobic terminal of an amino acid is increased by length in the high salt-resistance antibacterial peptide.

Preferably, the side chain of an amino acid increased by width and/or by length is increased by an aromatic amino acid.

Preferably, the aromatic amino acid for increasing the width of the side chain is with a width of a side chain of the aromatic amino acid between 4.659 Å to 8.924 Å.

Preferably, the aromatic amino acid is selected from the group of tryptophan (Trp), β-(benzothien-3-yl)alanine (Bal), β-(naphtha-1-yl)alanine (1-Nal), β-(naphtha-2-yl)alanine (2-Nal), β-diphenylalanine (Dip), β-(anthracen-9-yl)alanine (Ath) and β-(2,5,7-tri-tert-butyl-indol-3-yl)alanine (Tbt).

Preferably, the aromatic amino acid for increasing the length of the side chain is with a width of a side chain of the aromatic amino acid between 5.415 Å to 8.695 Å.

Preferably, the aromatic amino acid is selected from the group of tryptophan (Trp), β-(naphtha-2-yl)alanine (2-Nal), β-4'-biphenyl)alanine (Bip) and β-(2,5,7-tri-tert-butyl-indol-3-yl)alanine (Tbt).

Preferably, the aromatic amino acid is an artificial or a non-artificial amino acid, the result is showed as TABLE 5:

Preferably, the antibacterial peptide is a peptide of histidine-rich family.

Preferably, the peptide of histidine-rich family is a P-113 peptide (SEQ ID NO:1)

Preferably, the side chain of a hydrophobic terminal of an amino acid is histidine.

The present invention also provides a method for increasing the salt resistance of an antibacterial peptide which is by increasing the width of a side chain of a hydrophobic terminal in an amino acid and/or by increasing the length of a side chain of a hydrophobic terminal in an amino acid.

Preferably, the side chain of an amino acid increased by width and/or by length is increased by an aromatic amino acid.

Preferably, the aromatic amino acid for increasing the width of the side chain is with a width of a side chain of the aromatic amino acid between 4.659 Å to 8.924 Å.

Preferably, the aromatic amino acid is selected from the group of tryptophan (Trp), β-(benzothien-3-yl)alanine (Bal), β-(naphtha-1-yl)alanine (1-Nal), β-(naphtha-2-yl)alanine (2-Nal), β-diphenylalanine (Dip), β-(anthracen-9-yl)alanine (Ath) and β-(2,5,7-tri-tert-butyl-indol-3-yl)alanine (Tbt).

Preferably, the aromatic amino acid for increasing the length of the side chain is with a width of a side chain of the aromatic amino acid between 5.415 Å to 8.695 Å.

Preferably, the aromatic amino acid is selected from the group of tryptophan (Trp), β-(naphtha-2-yl)alanine (2-Nal), β-4'-biphenyl)alanine (Bip) and β-(2,5,7-tri-tert-butyl-indol-3-yl)alanine (Tbt).

Preferably, the aromatic amino acid is an artificial or a non-artificial amino acid.

Preferably, the antibacterial peptide is a peptide of histidine-rich family.

Preferably, the peptide of histidine-rich family is a P-113 peptide (SEQ ID NO:1)

Preferably, the side chain of a hydrophobic terminal of an amino acid is histidine.

In Summary, the present invention provides a high salt-resistance antibacterial peptide, and a method of increasing the salt resistance of an antibacterial peptide which is by increasing the width and/or the length of a side chain of a hydrophobic terminal in an amino acid in an amino acid, so as to evaluate the salt resistance of the antibacterial peptide.

DETAILED DESCRIPTION OF THE INVENTION

The present invention provides a high salt-resistance antibacterial peptide and a method of for increasing the salt resistance of an antibacterial peptide. Wherein the antibacterial peptide can be all known peptide includes but not limited to histidine-rich peptide; wherein the histidine-rich peptide is belonging to a histidine protein family. In the best embodiment, the histidine-rich peptide is belonging to a histidine protein family is P113 which sequence is AKRHH-GYKRKFH-NH$_2$ (SEQ ID NO: 1).

The antibacterial peptide in the present invention is synthesis artificially by peptide which is selected form artificial or non-artificial aromatic amino acid with large functional group. During the synthesis, the by substituting the original functional group of the amino acid to increase the width of the original functional group or the length of the original functional group, so as to increase the area or volume. The original functional group can be all kinds of amino acid, in the better embodiment, it is histidine. The increased length is between 5.415 Å-8.695 Å; and the increased width is between 4.659 Å-8.924 Å. Due to the increase of the length and/or width and the relative increase of area and volume. For achieve the criteria of the length and width above, the substitute functional group is from tryptophan (Trp), β-(benzothien-3-yl)alanine (Bal), β-(naphtha-1-yl)alanine (1-Nal), β-(naphtha-2-yl)alanine (2-Nal), β-diphenylalanine (Dip), β-(anthracen-9-yl)alanine (Ath) and β-(2,5,7-tri-tert-butyl-indol-3-yl)alanine (Tbt).

The antibacterial peptide in the present invention has high salt-resistance, and performs excellently antibacterial ability even in the environment that the concentration of NaCl is lager than 200 mL.

Generally, the antibacterial peptide includes peptide with 12-15 amino acids. P113 is used in the following example. The hydrophobic terminal of P113 is replaced by an artificial or a non-artificial aromatic amino acid with lager functional group, and then its antibacterial effect is tested.

For clarity of disclosure, and not by way of limitation, the detailed description of the invention is divided into the subsections that follow.

EXAMPLES

Example 1

Preparation of Phe-P113, Nal-P113 and Bip-P113

The Phe-P113, Nal-P113 and Bip-P113 is purchased from SynBioSci. Corp. (commercialized artificial peptide) and the purity is exceed 95% which is tested by MALDI-TOF.

Figure 1:
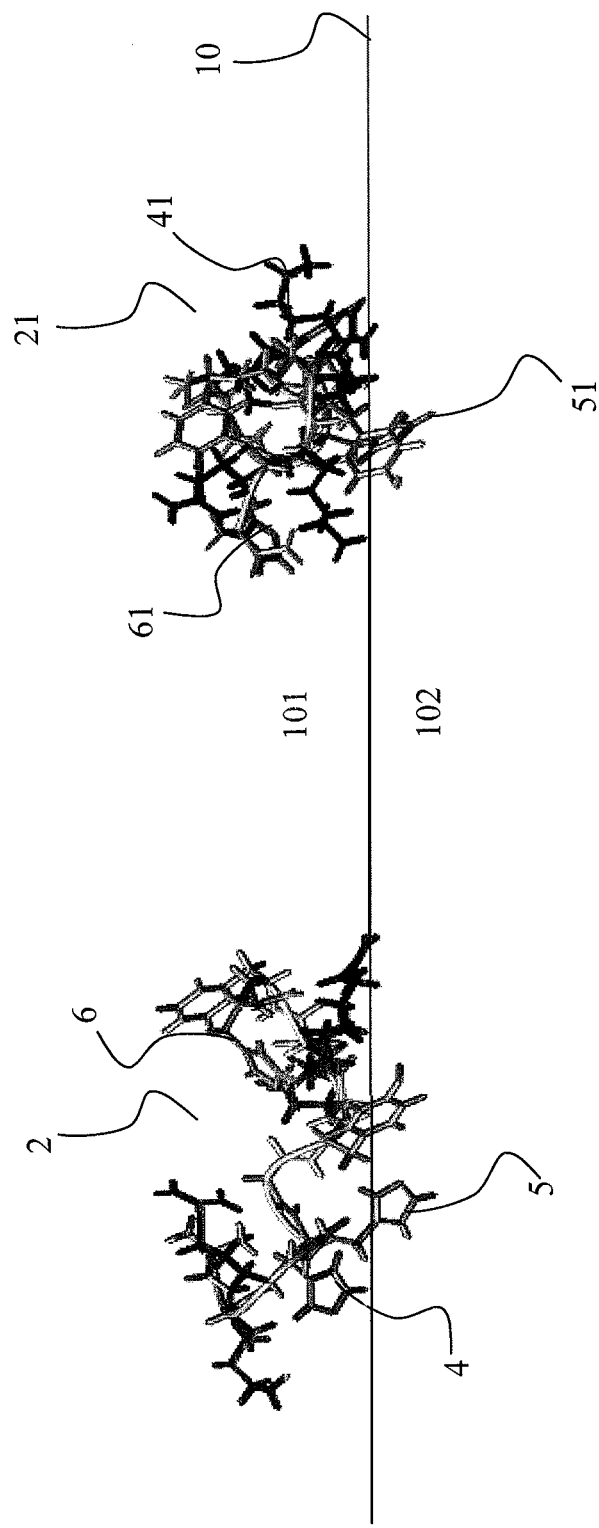
FIG. 1: The scheme of the surface of microbes invasive by antibacterial peptide P113, which is showed by lateral view and longitudinal view.
Figure 2:
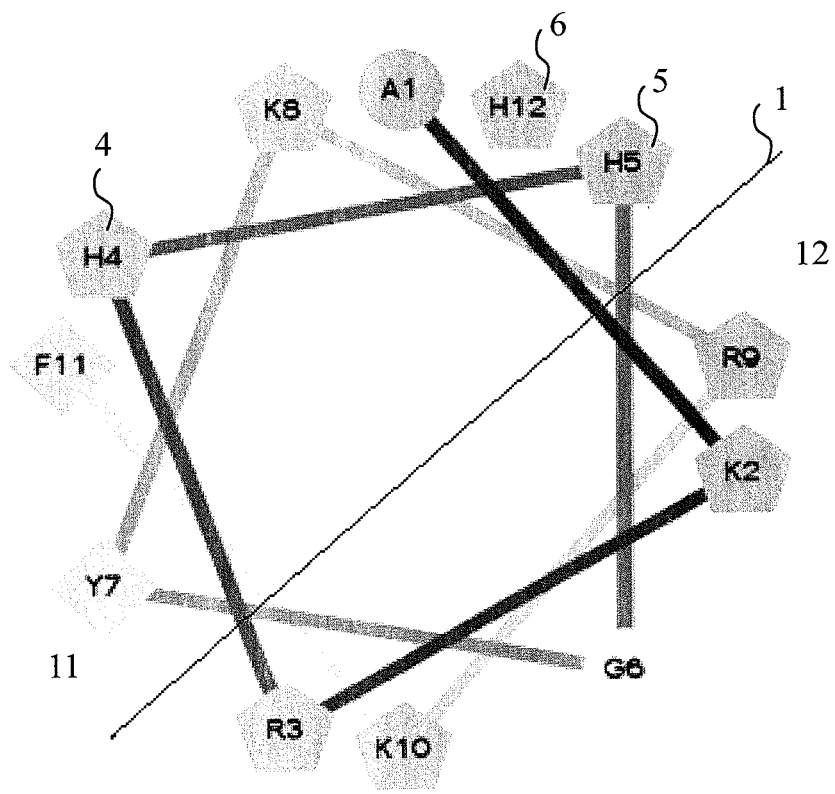
FIG. 2: The sectional view of α-helix structure of antibacterial peptide P113.

As shown in FIG. 2, the histidine of the His4 (4), His5 (5) and His12 (6) of hydrophobic terminal (11) in P113 is substituted by Phe(Phenylalanine, 2-Nal 2-Naphthylalanine and Bip[β-(4,4'-biphenyl)alanine during the synthesis. Wherein the Phe-P113 which is substituted by Phe is control group, and the Nal-P113 and Bip-P113 which is substituted by 2-Nal and Bip relatively is experimental group.

Figure 3:
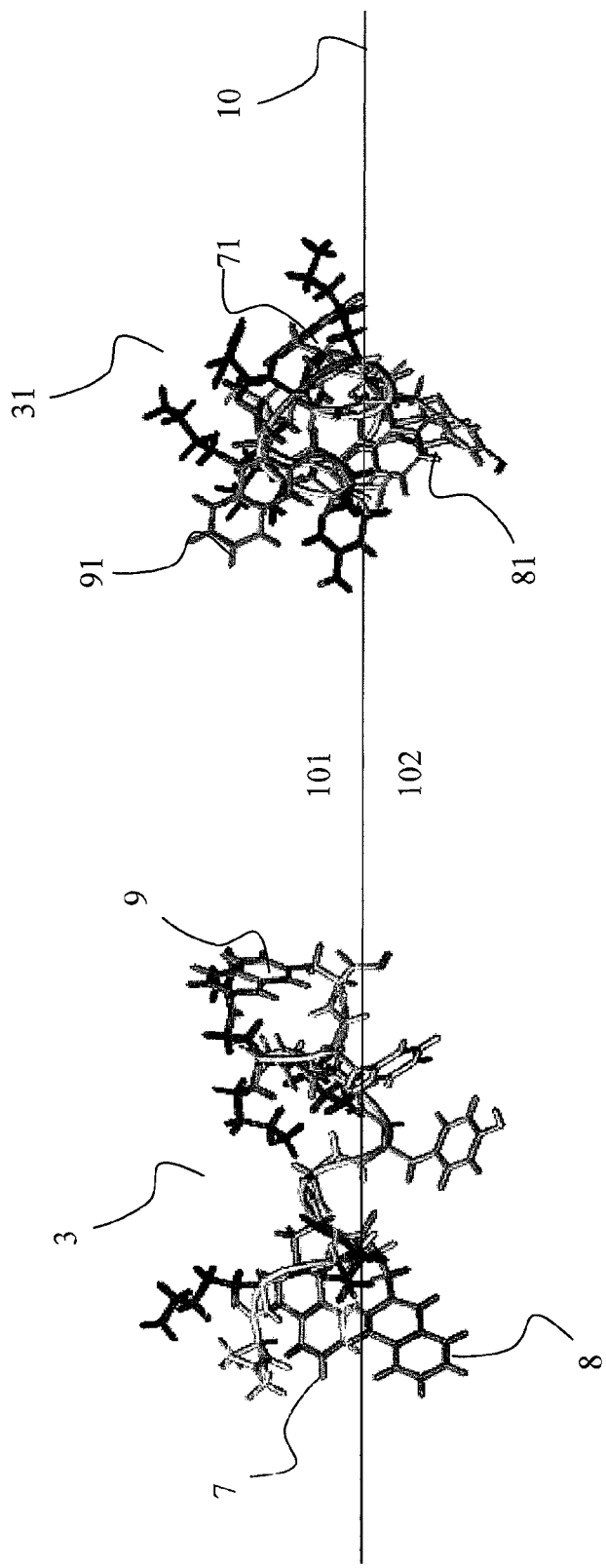
FIG. 3: The scheme of the surface of microbes invasive by antibacterial peptide P113.

The peptide structure is shown as FIG. 3, this is a mimic of Nal-P113 attached on the surface of a microbe and is a lateral sectional view of 3D structure of lateral structure (3) of Nal-P113 α-helix with longitudinal structure of P113 a-helix (31). The lateral line is cell membrane (10) of the surface of the microbe, and above this line is outside (101) of the microbe so is a hydrophilic environment, and beneath this line is the inner portion (102) of the microbe so is a hydrophobic environment. The His4, His5, His12 are replaced by artificial or non-artificial aromatic amino acid with lager functional group, such as 2-Nal. We find that the Nal-P113 (FIG. 3) can insert the surface of the microbe deeper to help itself stay on the surface of the microbe and enhance the antibacterial ability. Besides, the antibacterial ability of the Nal-P113 is better than P-113 in different concentration of salt.

Example 2

The Antibacterial Ability of Phe-P113, Nal-P113 and Bip-P113

For testing the antibacterial ability of Phe-P113, Nal-P113 and Bip-P113 in different salt concentration, we use Antibacterial activity assay to perform the test. Three bacteria strains are used: *Eschericha coli* strains (ATCC 25922), Staphylococcus aureus strains (ATCC 25923, 29213 and 19636, methicillin-resistant) and Pseudomonas aeruginosa strains (ATCC 27853 and 9027, ampicillin-resistant).

The microdilution method of National Committee for Clinical Laboratory Standards (NCCLS) is used to evaluate 'The minimal inhibition concentration (MIC)'. The minimum concentration that can inhibit 90% or more microbes is the 'minimal inhibition concentration'.

In the microdilution method, the 1 μl peptide solution (The concentration is between the range of 5000 μg/ml to 78.1 μg/ml) and the 99 μl inoculums (5×10^5 CFU/ml) is mixed incubated in 96-well culture dish coated with polyethylene under 37° C. for 16 hr. Then evaluated the turbidity in O.D.600 by ELISA plate reader (Thermo Max, Molecular Devices, Sunnyvale, Calif.). Take the Muller-Hinton Broth (MHB) and inoculums suspension with adding peptides as negative and positive control group relatively. The result of MIC is the minimum concentration of peptides that can inhibit the bacteria growth (equal to or more than 90%). All bacteria strains were tested for 3 times, the result is showed as TABLE 1:

TABLE 1

The test result of antibacterial ability of Phe-P113, Nal-P113 and Bip-P113

| Bacteria Strains | MHB | | | |
|---|---|---|---|---|
| | P113 | Phe-P113 | Nal-P113 | Bip-P113 |
| Eschericha coli strains ATCC 25922 | >50 | >50 | 12.5 | 12.5 |
| Staphylococcus aureus strains ATCC 25923 | >50 | >50 | 6.25 | 3.125 |
| Staphylococcus aureus strains ATCC 29213 | >50 | >50 | 6.25 | 6.25 |
| Staphylococcus aureus strains ATCC 19636 | >50 | >50 | 6.25 | 12.5 |
| Pseudomonas aeruginosa strains ATCC 27853 | >50 | >50 | 50 | 50 |
| Pseudomonas aeruginosa strains ATTC 9027 | >50 | >50 | 50 | 50 |

In summary, after replacing the His of P113 by Nal and Bi, the antibacterial ability is stronger than original P113.

Example 3

Evaluation the Antibacterial Ability of Phe-P113, Nal-P113 and Bip-P113 in Different Salt Concentration Then, evaluated the antibacterial ability of Phe-P113 (represented as Phe), Nal-P113 (represented as Nal) and Bip-P113 (represented as Bip) in different salt concentration. The result is showed as TABLE 2:

TABLE 2

Evaluation the antibacterial ability of Phe-P113, Nal-P113 and Bip-P113 in different salt concentration

| | | | E. coli ATCC 25922 | S. aureus ATCC 25923 | S. aureus ATCC 29213 | S. aureus ATCC 19636 | P. arugenosa ATCC 27853 | P. arugenosa ATCC 9027 |
|---|---|---|---|---|---|---|---|---|
| Control group | | P113 | 12.5 | 12.5 | 12.5 | 50 | 25 | 12.5 |
| | | Phe | 12.5 | 6.25 | 6.25 | 25 | 25 | 25 |
| | | Nal | 3.125 | 1.56 | 1.56 | 6.25 | 1.56 | 3.125 |
| | | Bip | 6.25 | 3.125 | 3.125 | 6.25 | 3.125 | 3.125 |
| NaCl | 50 mM | P113 | 50 | 50 | 50 | 50 | 50 | 50 |
| | | Phe | 50 | 12.5 | 12.5 | 50 | 50 | >50 |
| | | Nal | 3.125 | 1.56 | 1.56 | 12.5 | 1.56 | 6.25 |
| | | Bip | 6.25 | 3.125 | 3.125 | 6.25 | 3.125 | 3.125 |
| | 100 mM | P113 | 50 | 50 | 50 | 50 | 50 | 50 |
| | | Phe | >50 | 50 | 50 | >50 | 50 | >50 |
| | | Nal | 12.5 | 3.125 | 3.125 | 25 | 12.5 | 50 |
| | | Bip | 6.25 | 6.25 | 3.125 | 6.25 | 6.25 | 6.25 |
| | 200 mM | P113 | >50 | >50 | >50 | >50 | >50 | >50 |
| | | Phe | >50 | >50 | >50 | >50 | >50 | >50 |
| | | Nal | 25 | 12.5 | 6.25 | 50 | 50 | 50 |
| | | Bip | 12.5 | 6.25 | 3.125 | 12.5 | 6.25 | 6.25 |
| | 300 mM | P113 | >50 | >50 | >50 | >50 | >50 | >50 |
| | | Phe | >50 | >50 | >50 | >50 | >50 | >50 |
| | | Nal | 50 | 50 | 25 | 50 | >50 | >50 |
| | | Bip | 12.5 | 25 | 12.5 | 12.5 | 12.5 | 50 |

All bacteria strains of above microbes were cultured in LYM medium. LYM is a low salt concentration culture medium which is used to test the antibacterial ability of antibacterial peptide with lower salt-resistance ability. The NaCl concentrations in LYM were divided into four groups of 50 mM, 100 mM, 200 mM, 300 mM and the microbes were cultured in the four group of LYM and diluted to a $10^4$ CFU/ml bacterial solution. Then added 100 μl of the bacterial solution into 96-well culture dish and added different concentration of antibacterial peptides P113, Phe-P113, Nal-P113 or Bip-P113 to evaluate the antibacterial ability in 50 mM, 100 mM, 200 mM, 300 mM concentration of NaCl. (Note: In addition to NaCl, the LYM medium also contains 5.4 mM KCl, 5.6 mM $Na_2HPO_4$, 0.5 mM $MgSO_4$, and 1.0 mM sodium citrate. Besides, 0.4 mg of $ZnCl_2$, 2.0 mg of $FeCl_3 \cdot 6H_2O$, 0.1 mg of $CuSO_4 \cdot 5H_2O$, 0.1 mg of $MnSO_4 \cdot H_2O$, 0.1 mg of $Na_2B_4O_7 \cdot 10H_2O$, 700 mg of amino acid mixtures without tryptophan (Clontech), and 20 mg of L-Tryptophan were added per liter of medium. Then added moderate amount of glucose, amino acid, and vitamins mixture from the RPM1-1640 Select-Amine Kit)

In brief summary, in different concentration of NaCl, Nal-P113 and Bip-P113 remains their activity of antibacterial.

Example 4

Evaluation the Antibacterial Ability of Phe-P113, Nal-P113 and Bip-P113 in Different MgCl2 Concentration Evaluating the antibacterial ability of Phe-P113, Nal-P113 and Bip-P113 in different MgCl2 concentration, the result is showed as TABLE 3.

TABLE 3

Evaluation the antibacterial ability of Phe-P113, Nal-P113 and Bip-P113 in different MgCl2 concentration
Bacteria strains

| | | | E. coli ATCC 25922 | S. aureus ATCC 25923 | S. aureus ATCC 29213 | S. aureus ATCC 19636 | P. arugenosa ATCC 27853 | P. arugenosa ATCC 9027 |
|---|---|---|---|---|---|---|---|---|
| Control group | | P113 | 12.5 | 12.5 | 12.5 | 50 | 25 | 12.5 |
| | | Phe | 12.5 | 6.25 | 6.25 | 25 | 25 | 25 |
| | | Nal | 3.125 | 1.56 | 1.56 | 6.25 | 1.56 | 3.125 |
| | | Bip | 6.25 | 3.125 | 3.125 | 6.25 | 3.125 | 3.125 |
| $MgCl_2$ | 0.5 mM | P113 | 12.5 | 50 | 12.5 | >50 | 50 | >50 |
| | | Phe | 25 | 6.25 | 6.25 | 25 | 50 | 50 |
| | | Nal | 3.125 | 3.125 | 1.56 | 12.5 | 3.125 | 6.25 |
| | | Bip | 6.25 | 3.125 | 3.125 | 6.25 | 3.125 | 3.125 |
| | 1.5 mM | P113 | 25 | 50 | 25 | >50 | 50 | >50 |
| | | Phe | 50 | >50 | 12.5 | 25 | >50 | 50 |
| | | Nal | 6.25 | 3.125 | 1.56 | 12.5 | 3.215 | 6.25 |
| | | Bip | 6.25 | 3.125 | 3.125 | 6.25 | 6.25 | 6.25 |
| | 2.5 mM | P113 | 25 | 50 | 25 | >50 | 50 | >50 |
| | | Phe | >50 | >50 | >50 | 50 | >50 | >50 |
| | | Nal | 12.5 | 3.125 | 1.56 | 25 | 6.25 | 12.5 |
| | | Bip | 6.25 | 3.125 | 3.125 | 6.25 | 12.5 | 6.25 |

Example 5

Evaluation the Sensitivity of Fluconazole, P113 and Nal-P113 to Fungus Candida spp.

TABLE 4

Evaluation the sensitivity of fluconazole, P113 and Nal-P113 to fungus Candida spp.

| Fungi strains | origin | Strain | Flu | Control group P-113 | Nal | 50 mM NaCl P-113 | Nal | 100 mM NaCl P-113 | Nal | 150 mM NaCl P-113 | Nal |
|---|---|---|---|---|---|---|---|---|---|---|---|
| C. krusei | ATCC 6258 | YLO6 | 32* | 6.25 | 6.25 | 6.25 | 6.25 | 100 | 6.25 | 100 | 12.5 |
| C. parapsilosis | ATCC 22019 | YLO7 | 8 | 6.25 | 6.25 | 50 | 12.5 | >100 | 12.5 | >100 | 25 |
| C. glabrata | ATCC 9003 | YLO8 | 16 | 12.5 | 6.25 | >100 | 25 | >100 | 25 | >100 | 25 |
| C. albicans | ATCC 90028 | YLO12 | 1 | 6.25 | 6.25 | 25 | 12.5 | 100 | 12.5 | >100 | 12.5 |
| C. tropicalis | ATCC 13803 | YLO86 | >64 | 3.1 | 6.25 | 3.1 | 6.25 | 12.5 | 6.25 | 12.5 | 6.25 |
| C. albicans | HIV patient | YHO50001 | 2 | 6.25 | 6.25 | 25 | 12.5 | 100 | 12.5 | >100 | 12.5 |
| C. albicans | HIV patient | YHO50005 | 1 | 6.25 | 6.25 | 50 | 25 | >100 | 25 | >100 | 25 |
| C. tropicalis | HIV patient | YHO50007 | >64 | 3.1 | 6.25 | 3.1 | 6.25 | 25 | 6.25 | 25 | 12.5 |
| C. tropicalis | HIV patient | YHO50013 | >64 | 3.1 | 6.25 | 3.1 | 6.25 | 50 | 6.25 | 50 | 12.5 |
| C. albicans | HIV patient | YHO50072 | >64 | 6.25 | 6.25 | 25 | 25 | >100 | 25 | >100 | 25 |
| C. krusei | HIV patient | YHO50075 | 64 | 6.25 | 6.25 | 25 | 12.5 | >100 | 12.5 | >100 | 12.5 |
| C. dubliniensis | HIV patient | YHO50092 | 0.5 | 6.25 | 6.25 | 12.5 | 12.5 | >100 | 12.5 | >100 | 12.5 |

TABLE 4-continued

Evaluation the sensitivity of fluconazole, P113 and Nal-P113 to fungus Candida spp.

| Fungi strains | origin | Strain | Flu | Control group | | 50 mM NaCl | | 100 mM NaCl | | 150 mM NaCl | |
|---|---|---|---|---|---|---|---|---|---|---|---|
| | | | | P-113 | Nal | P-113 | Nal | P-113 | Nal | P-113 | Nal |
| C. glabrata | HIV patient | YHO50105 | 16 | 6.25 | 6.25 | 50 | 12.5 | 100 | 25 | >100 | 50 |
| C. tropicalis | HIV patient | YHO50114 | >64 | 3.1 | 6.25 | 3.1 | 6.25 | 100 | 6.25 | 100 | 12.5 |

*MIC (μg mL$^{-1}$); Flu: fluconazole.

In typical LYM culture medium, the sensitive effects of P113 and Nal-P113 to fungus are no big difference. However, flu is the control group in low salt concentration environment. The concentration is higher of flu than P113 and Nal-P113 to induce the sensitivity of fungus. With increasing of the NaCl concentration, the concentration of P113 to induce the sensitivity of fungus is higher. The Nal-P113 concrete effect is showed in both In Vitro and HIV patients data (TABLE 4).

Example 6

Replacing by the Aromatic Amino Acid of Functional Group with Different Length and Width As shown in examples 1-5, when the His of P113 is replaced by wider or longer functional group, the degree of resist the variation of salt concentration would be evaluated.

The substitute functional groups can be artificial or non-artificial aromatic amino acid with large functional group. When the length is longer than Trp group and longer than 4.659 Å, it is belonged to the candidate amino acid used to increase the length such as Trp, 2-Nal, Bip, Tbt in the length column of the TABLE 5. When the width is wider than Trp group and longer than 5.415 Å, it is belonged to the candidate amino acid used to increase the length such as Trp, Bal, 1-Nal, 2-Nal, Dip, Ath, Tbt in the length column of the TABLE 5.

TABLE 5

The structure feature of the artificial or non-artificial aromatic amino acid with large functional group

| Amino acid | Volume (Å$^3$) | Area (Å$^2$) | Length$^a$ (Å) | Width$^b$ (Å) |
|---|---|---|---|---|
| Phe | 100 | 274.6 | 4.341 | 2.429 |
| Trp | 129.4 | 318.9 | 5.415 | 4.659 |
| Bal | 135 | 324.4 | 5.35 | 4.796 |
| 1-Nal | 142.1 | 333.8 | 5.185 | 4.976 |
| 2-Nal | 142.6 | 340 | 6.476 | 4.973 |
| Bip | 172.3 | 391.8 | 8.695 | 2.429 |
| Dip | 172.4 | 387.9 | 4.343 | 7.119 |
| Ath | 185.4 | 391.3 | 5.141 | 7.274 |
| Tbt | 325.1 | 580.5 | 7.6 | 8.924 |

$^a$the largest distance of length between any two carbon atoms on the side chain of the amino acid
$^b$the largest distance of width between any two carbon atoms on the side chain of the amino acid As shown in TABLE 5, three amino acid can meet on both length and width requirement: Trp, 2-Nal and Tbt.

In summary, the present invention provides an antibacterial peptide with high salt-resistance and provides a method for increasing the salt resistance of antibacterial peptide to solve the problem that the salt-resistance of antibacterial peptide is low.

What is claimed is:

1. A high salt-resistance antibacterial peptide, wherein the high salt-resistance antibacterial peptide is modified P-113 peptide (SEQ ID NO:1), wherein the His4, His5, and/or His12 of P-113 peptide (SEQ ID NO:1) has been replaced/substituted with an aromatic amino acid,
wherein the aromatic amino acid is selected from the group of β-(benzothien-3-yl)alanine (Bal), β-(naphtha-1-yl)alanine (1-Nal), β-(naphtha-2-yl)alanine (2-Nal), β-diphenylalanine (Dip), β-(anthracen-9-yl)alanine (Ath), β-(4,4'-biphenyl)alanine (Bip), and β-(2,5,7-tri-tert-butyl-indol-3-yl)alanine (Tbt).

2. A high salt-resistance antibacterial peptide, wherein the high salt-resistance antibacterial peptide is a modified P-113 peptide (SEQ ID NO:1), wherein the His4, His5, and/or His12 of P-113 peptide (SEQ ID NO:1) has been replaced/substituted with an aromatic amino acid,
wherein the aromatic amino acid is selected from the group of β-(benzothien-3-yl)alanine (Bal), β-(naphtha-1-yl)alanine (1-Nal), β-(naphtha-2-yl)alanine (2-Nal), β-diphenylalanine (Dip), β-(anthracen-9-yl)alanine (Ath), β-(4,4'-biphenyl)alanine (Bip), and β-(2,5,7-tri-tert-butyl-indol-3-yl)alanine (Tbt).

3. A method for producing a high-salt resistance antibacterial peptide comprising: providing antibacterial peptide P-113 (SEQ ID NO:1); and replacing/substituting the His4, His5, and/or His12 of P-113 peptide (SEQ ID NO:1) with an aromatic amino acid to thereby produce a high-salt resistance antibacterial peptide,
wherein the aromatic amino acid is selected from the group of β-(benzothien-3-yl)alanine (Bal), β-(naphtha-1-yl)alanine (1-Nal), β-(naphtha-2-yl)alanine (2-Nal), β-diphenylalanine (Dip), β-(anthracen-9-yl)alanine (Ath), β-(4,4'-biphenyl)alanine (Bip), and β-(2,5,7-tri-tert-butyl-indol-3-yl)alanine (Tbt).

4. A method for producing a high-salt resistance antibacterial peptide comprising: providing antibacterial peptide P-113 (SEQ ID NO:1); and replacing/substituting the His4, His5, and/or His12 of P-113 peptide (SEQ ID NO:1) with an aromatic amino acid to thereby produce a high-salt resistance antibacterial peptide,
wherein the length of the side chain of the aromatic amino acid is between 5.415 A and 8.695 A.

5. The method for producing a high-salt resistance antibacterial peptide according to claim 4, wherein the aromatic amino acid is selected from the group of β-(naphtha-2-yl)alanine (2-Nal), β-(4,4'-biphenyl)alanine (Bip) and β-(2,5,7-tri-tert-butyl-indol-3-yl)alanine (Tbt).

* * * * *